(12) United States Patent
Galli et al.

(10) Patent No.: US 9,835,560 B2
(45) Date of Patent: Dec. 5, 2017

(54) METHOD AND DEVICE FOR THE RAMAN SPECTROSCOPIC, IN OVO SEX DETERMINATION OF FERTILISED AND INCUBATED BIRDS' EGGS

(71) Applicants: TECHNISCHE UNIVERSITAET DRESDEN, Dresden (DE); UNIVERSITAET LEIPZIG, Leipzig (DE)

(72) Inventors: Roberta Galli, Dresden (DE); Grit Preusse, Radebeul (DE); Edmund Koch, Dresden (DE); Gerald Steiner, Schwarzenberg (DE); Maria-Elisabeth Krautwald-Junghanns, Markleeberg (DE); Thomas Bartels, Gehrden (DE)

(73) Assignees: TECHNISCHE UNIVERSITAET DRESDEN, Dresden (DE); UNIVERSITAET LEIPZIG, Leipzig (DE)

( * ) Notice: Subject to any disclaimer, the term of this patent is extended or adjusted under 35 U.S.C. 154(b) by 0 days.

(21) Appl. No.: 15/317,802

(22) PCT Filed: Jul. 3, 2015

(86) PCT No.: PCT/DE2015/000342
§ 371 (c)(1),
(2) Date: Mar. 27, 2017

(87) PCT Pub. No.: WO2016/000678
PCT Pub. Date: Jan. 7, 2016

(65) Prior Publication Data
US 2017/0205353 A1    Jul. 20, 2017

(30) Foreign Application Priority Data
Jul. 4, 2014  (DE) .................. 10 2014 010 150

(51) Int. Cl.
*G01J 3/44* (2006.01)
*G01N 21/65* (2006.01)
(Continued)

(52) U.S. Cl.
CPC ............. *G01N 21/65* (2013.01); *G01N 33/08* (2013.01); *G01N 33/4833* (2013.01); *G01N 2021/653* (2013.01); *G01N 2201/06113* (2013.01)

(58) Field of Classification Search
CPC ........... G01J 3/44; G01N 33/48; G01N 33/08; G01N 21/65; G01N 21/00
See application file for complete search history.

(56) References Cited

U.S. PATENT DOCUMENTS

| 6,029,080 A | 2/2000 | Reynnells et al. |
| 6,365,339 B1 | 4/2002 | Daum et al. |

(Continued)

FOREIGN PATENT DOCUMENTS

| DE | 10 2007 013 107 | 9/2008 |
| DE | 10 2010 006 161 | 1/2011 |

(Continued)

OTHER PUBLICATIONS

Klein, "Analysis of chicken embryonic development after removal of blastodermal cells for sexing", British Poultry Science (39), 1998, pp. 482-487.

(Continued)

*Primary Examiner* — Abdullahi Nur
(74) *Attorney, Agent, or Firm* — Greenblum & Bernstein, P.L.C.

(57) ABSTRACT

The invention relates to a method for the Raman spectroscopic, in ovo sex determination of fertilized and hatched birds' eggs (1), wherein the embryo, including the extra-embryonic structures, can move in the egg, and is not yet (Continued)

attached to the shell at the time of measuring. In addition, the following steps are carried out: monitoring the time course of the hatched egg until forming at least one recognizable blood vessel (21); creating a hole (2) in the shell in the region near to the attached bloody vessel, using a hole-generating unit; finding the blood vessel forming in the egg, using a vision system (19, 13) and a coaxial or lateral illumination with light (10*a*) in the visible wavelength range; positioning at least one blood vessel in the laser focus of a laser source (3), either by moving the egg or moving a lens (6) of a device (5) for introducing the laser light (3*a*), and detecting the Raman scattered radiation (7); registering the Raman scattered radiation of the irradiated blood vessel using the device for introducing the laser light, and for detecting the Raman scattered radiation, wherein, during the measuring process, a movement of the blood vessel out of the focus can be avoided by tracking using the vision system; evaluating the Raman scattered radiation in an evaluation unit; determining and displaying the sex of the embryo in the bird's egg.

39 Claims, 5 Drawing Sheets (51) Int. Cl.
*G01N 33/483* (2006.01)
*G01N 33/08* (2006.01)

(56) References Cited

U.S. PATENT DOCUMENTS

| | | | |
|---|---|---|---|
| 6,506,570 B1 | 1/2003 | Phelps | |
| 7,041,439 B2 | 5/2006 | Phelps et al. | |
| 7,950,349 B1 | 5/2011 | Rollins | |
| 8,364,247 B2 | 1/2013 | Opitz et al. | |
| 2006/0095980 A1* | 5/2006 | Petitte | A01K 67/0271 800/19 |
| 2012/0058052 A1 | 3/2012 | Decuypere et al. | |
| 2013/0044210 A1 | 2/2013 | Rozenboim et al. | |
| 2015/0260704 A1 | 9/2015 | Bruins et al. | |

FOREIGN PATENT DOCUMENTS

| | | |
|---|---|---|
| DE | 10 2012 023 947 | 6/2014 |
| DE | 20 2013 011 765 | 7/2014 |
| EP | 2336751 | 6/2011 |
| WO | 2010/103111 | 9/2010 |
| WO | 2010/150265 | 12/2010 |
| WO | 2014/021715 | 2/2014 |

OTHER PUBLICATIONS

Brake et al., "Egg handling and storage," Poultry Science (76), 1997, pp. 144-151.
Volkmer, "Vibrational imaging and microspectroscopies based on coherent anti-Stokes Raman scattering microscopy", Appl. Phys. 38 10.1088/0022-3727/38/5/R01, 2005, pp. R59-R81.
Dogariu et al., "Sensitive femtosecond CARS discrimination between 2,6 Dipicolinic acid and 3,5 Dipicolinic acid", Opt. Lett., vol. 31, No. 21, 2006, pp. 3176.
Huang et al. "Backscattered Coherent Anti-Stokes Raman Scattering for At Range Detection of Dipicolinic Acid and Four-Wave Mixing Multiple Scattering", J. Mod. Optics vol. 54, No. 16, 2007, pp. 2473.
A. Dogariu et al., "Real-time detection of bacterial spores using Coherent anti-Stokes Raman Spectroscopy", J. Appl. Phys. 103, 2008, pp. 1-4.
A. Dogariu et al., "Coherent Anti-Stokes Raman Spectroscopy for detecting explosives in real-time", Proc. of SPIE vol. 8358, pp. 1-9.
A. Dogariu et al., "Real-time montoring of blood using coherent anti-Stokes Raman spectroscopy", J. Biomed. Opt. 13, 2008, pp. 1-4.
Rinia et al., "Spectroscopic analysis of the oxygenation state of hemoglobin using coherent anti-stokes raman scattering", J. Biomed. Opt. 11(5), 2006, pp. 1-3.
Dmitry Pestov et al., "Single-shot Detection of Bacterial Endospores via Coherent Raman Spectroscopy", Proc. Nat. Acad. Sci. USA 105, 2008, pp. 422-427.

\* cited by examiner

METHOD AND DEVICE FOR THE RAMAN SPECTROSCOPIC, IN OVO SEX DETERMINATION OF FERTILISED AND INCUBATED BIRDS' EGGS

The invention relates to a method and a device for the Raman spectroscopic in ovo sex determination of fertilized and incubated birds' eggs.

In the document DE 10 2010 006 161 B3, a method and a device for determining the sex of fertilized and non-incubated birds' eggs are described, wherein an egg comprises at least a solid shell, an egg yolk surrounded by the shell and other egg integuments, and a germinal disc associated with the egg yolk, wherein a probe for measuring a spectrum is guided through a hole in the shell in the direction of the germinal disc having germinal disc cells, wherein the method comprises the following steps:

- a positioning of the probe in the region of the germinal disc,
- a spectroscopic in ovo characterization of the germinal disc cells,
- a detection of the sex by means of an automatic classification of the reflective spectra, wherein an optical crystal is used as a probe, with which crystal a rapid and feedback-free recording of an infrared and/or near-infrared spectrum is performed through the evanescent field in the region of the germinal disc with the use of the attenuated total reflection inside the optical crystal,
wherein the extinction takes place as a result of a spectral absorption of sex-specific germinal disc cells,
wherein the positioning of the optical crystal is accompanied by a continuous automatic evaluation of the back-guided spectra until the sex-specific germination disc cells are determined, until the spectrum is evaluated and the sex of the fertilized egg is displayed unequivocally.

During the positioning process, continuously back-guided IR and/or NIR spectra are recorded and supplied to an evaluation, wherein an automatic classification of the spectra takes place using the spectral fingerprint, for example in proteins, lipids and nucleic acids.

In the sex-specific absorption of the incident IR and/or NIR light, the germinal disc cells are identified using absorption bands of the nucleic acids (DNA and RNA) and other biochemical compounds such that the sex of the examined egg is determined and displayed.

The measurement can be conducted using conventional infrared spectroscopy.

The related device described in the document DE 10 2010 006 161 B3 comprises

- at least one egg position support for securing at least one egg,
- at least one height-adjustment device having at least one supporting arm,
- at least one optical crystal embodied as a probe, which crystal is attached to the supporting arm,
- at least one control unit for the egg-securing egg position support and for the height-adjustment device,
- at least one spectral light source related to at least one wavelength range which emits an IR and/or NIR light beam,
- at least one detector for receiving the back-guided IR and/or NIR light beam,
- at least one optical element for the beam guidance guided between the light source and the optical crystal and for the beam guidance back-guided from the optical crystal to the detector, and
- one evaluation unit connected to the detector, as well as a display unit, wherein by means of the height-adjustment device the height of the supporting arm, and thus of the optical crystal, is adjustable in relation to the location of the germinal disc, and the optical crystal is positionable in the region of the germinal disc in a disc mapping position, in which an evanescent field which forms during total reflection at the output surface oriented toward the germinal disc is transferred to the germinal disc by means of the optical crystal, and the germinal disc cells located therein absorb in a sex-specific manner the light from the incident beam path interactively with the evanescent field, wherein the light totally reflected at the output surface is guided via the back-guided beam path within the crystal and is then guided via the optical element to the detector for recording, from which detector the recorded spectral signals for the analysis and display of the sex are transmitted.

In the document DE 10 2007 013 107 A1, a DNA-relevant cell material is analyzed using vibrational spectroscopy in order to determine the sex of birds' eggs based on DNA differences: either in the egg opened using a probe, or after extraction of the material from the egg and deposition on a substrate. The UV resonance Raman spectroscopy is specified for wavelengths of 244 nm or 254 nm. A spectral classification is thereby carried out using all existing supervised and unsupervised methods:

- with a DNA-relevant material, with a special reference to the feather pulp and the germinal disc, and
- UV Raman spectroscopy at a wavelength of 244 nm or 257 nm.

In this method, DNA-relevant cell material of the bird for which the sex is to be determined is thus examined using light and the molecular vibrations are measured, wherein the spectrum of the molecular vibrations produced by the light is detected and compared with predefined reference spectra as well as reference spectra representing sex-specific DNA structures of the bird species being examined, and wherein from said spectral comparison a sex is assigned to the bird based on the DNA content of the cell material.

The molecular vibrations are thereby measured using Raman spectroscopy or IR spectroscopy, wherein for example the DNA-relevant cell material can be extracted from the shaft of a young feather. The cell material is prepared on a slide and scanned using light.

In another partial method described in the document DE 10 2007 013 107 A1, the light for measuring the molecular vibrations of the DNA-relevant cell material of unhatched birds is focused on the embryo or the germinal disc through the egg shell, wherein the spectrum of the radiation in the egg produced by the molecular vibrations is measured using a probe guided through the shell of said egg.

In order to guide the probe, at least one microscopically small hole is drilled through the egg shell to measure the spectrum. The light is focused through the small access point through the egg shell directly onto the germinal disc serving as cell material. The probe is inserted through the same access point or a different access point having a small opening size, by means of which probe the reflected spectrum of the aforementioned molecular motion in the interior of the egg, which spectrum is recorded by the probe, is measured.

The spectral information obtained is, in a second step, compared with sex-specific reference data and supplied to a classification algorithm. Said data preferably represent statistically acquired data about the bird species being analyzed. From this comparison, a sex is assigned to the DNA material being analyzed.

One problem is that a significant cost in terms of time is required to insert a probe into preformed holes if a very high number of birds' eggs are to be analyzed. In addition, when the light from the probe is focused onto the germinal disc, considerable adjustment work must be performed for an optical mapping in relation to the location of the germinal disc, wherein the focal plane can have a different position for each egg, and it is thus not possible to carry out a sex determination.

A further problem with these analyses is that the creation of the holes in the shell, including the egg shell membrane, at day "zero" required to analyze the germinal discs results in an impairment of the embryonic development and in markedly decreasing hatching rates, as is described in the documents S. Klein: Analysis of chicken embryonic development after removal of blastodermal cells for sexing. British Poultry Science (39), 1998, p. 482-487; including the literature cited therein: J. Brake, T. W. (1997). Egg handling and storage. Poultry Science (76), p. 144-151.

In the document WO 2014/021715 A2, a sex determination of bird embryos is described, wherein the method is carried out by means of
a) a detection of a marker compound of sugars and amino acids, precursors and metabolites in the allantoic fluid of the egg at the eight to eleventh day of incubation,
b) a quantitative determination of the marker using NMR spectroscopy,
c) a sex determination by comparing the quantity of the marker to a predefined base value.

The following thereby take place:
  a determination of the absolute quantities or proportions of compounds (glucose, choline, valine) in order to compare them with a base value,
  an application of unsupervised chemometric methods (such as least-square modeling or PCA) to quantitative amounts or proportions for the purpose of sex determination.

A major disadvantage of the method is that at least one sample is taken from the egg.

In the documents U.S. Pat. No. 8,364,247 B2 and EP 2 336 751 A1, a method for determining the sex of birds' eggs is described in which, using a radiation source, electromagnetic radiation is emitted onto the germinal disc of an egg, and after switching off the radiation source the decay process of the excited inherent fluorescence intensity is detected at the irradiated region of the germinal disc in a time-resolved and spectrally resolved manner for at least one wavelength of the inherent fluorescence using a detector. Using the determined measured intensity values, the fractal dimension is calculated and the value of the fractal dimension DF is compared with a species- and sex-specific limit value; wherein the respective egg is classified as female if the limit value is exceeded and male if the value is lower than the limit value.

The opening of the egg at day "zero" results in markedly reduced hatching rates. Furthermore, there is potential irreparable damage to the germinal disc from the 337 nm UV radiation used.

In the document U.S. Pat. No. 7,950,349 B1, a method for determining:
1) the fertility of a bird egg by measuring the luminescence and the biophoton intensity (photons per second) of the egg after exposure to an external light source and
2) the sex of a bird egg by measuring the photon spectrum of the biophoton emission and luminescence of the egg after exposure to an external light source is described.

The external light source can thereby be either an incandescent lamp, fluorescent lamp, an LED, or a (pulsed or CW) monochromatic or dichromatic laser light source. The first part of the method results from the fact that, following exposure using the light source, the fertile birds' eggs emit a higher intensity of the photons than that emitted by the unfertilized birds' eggs. The second part of the method results from the fact that, following exposure using the indicated light sources, birds' eggs of the female sex emit a different spectrum of photons than birds' eggs of the male sex.

In the documents WO 2010/103111 A1 and US 2012/0058052 A1, a non-invasive method and a device for the in ovo sex determination of bird species are described. The method comprises the steps of introducing a marked antibody into the egg, which antibody binds to a sex-specific antigen of the embryo, and the detection of the marked bound antibody using a detection device outside the egg.

In the document U.S. Pat. No. 7,041,439 B2, a method and a device for automated process management of eggs according to selected characteristics (for example, sex) are described, wherein the following steps take place:
a) an extraction of sample material (allantoic fluid, egg white, egg yolk, egg shell, albumin, tissue, membrane, and/or blood),
b) an analysis of the extracted material to determine the selected characteristics, and
c) selective process management for the identified eggs. or example, a method for processing eggs based on the sex is described therein, which method comprises the following steps:
1) an identification of living eggs,
2) an extraction of allantoic fluid from the eggs identified as living,
3) a determination of the estrogen content and of a color change in the extracted allantoic fluid for the purpose of sex determination,
4) a selective injection of a vaccine depending on the sex.

One disadvantage is that the analysis of the allantoic fluid takes place at day 13 through 18.

Sampling is also necessary in this case.

In the document U.S. Pat. No. 6,365,339 B1, a method for the sex determination of bird embryos is described in which, during the incubation process, samples are taken from the allantoic fluid of the embryo after the shell is drilled open and are analyzed in an ion mobility spectrometer (IMS). The resulting spectra contain relevant marker peaks which correlate with sex-specific mobilities. One disadvantage is that samples must also be taken in this case, which samples necessitate a higher cost at least in the context of the sex determination.

In the documents WO 2010/150265 A3 and US 2013/0044210 A1, a method for the sex determination of non-incubated birds' eggs by means of a hyperspectral analysis of optical spectra (preferably reflection spectra) is described. The analysis takes place in a spectral range with wavelengths up to 2500 nm (MIR) in order to be able to filter out the signal generated by the $CaCO_3$ of the egg's shell at 2340 nm. The method enables the detection of biological components other than blood, and renders possible both the detection of fertility before the second incubation day and also the determination of the sex of the chicks in the egg at the twelfth incubation day. It was possible to increase the sensitivity through the use of a neuronal network analysis.

By means of principal component analysis (PCA), the spectral characteristics that are responsible for the variances between the unfertilized control eggs and the sample eggs are determined. By employing a neuronal network analysis based on the PCA results, the small yet significant variances between the control eggs and experimental eggs are then obtained. The method enables the determination of fertility with an accuracy of more than 90% at day "zero" (date of egg laying), and of the sex of the chicks with an accuracy of over 75% at the twelfth incubation day.

One disadvantage is that, with this method, a sex determination cannot be carried out until the twelfth day.

In the document U.S. Pat. No. 6,029,080 B1, a non-invasive method and a device for the sex determination of birds' eggs is shown in which nuclear magnetic resonance (NMR) is used to determine whether the living embryo in the egg has male sex organs or female sex organs.

One disadvantage is that the formation of the sex organs only takes place in a developed embryo after several essential days, wherein at least the implementation requires a high financial cost.

In the document U.S. Pat. No. 6,506,570 B1, the presence or absence of an elevated sex-specific hormone level, preferably the estrogen level, is determined in an extra-embryonic fluid, preferably the allantoic fluid, for the purpose of in ovo sex determination. The method is preferably applied to chicken eggs and can be carried out before or during the transfer from the incubator to the hatcher.

In the document DE 10 2012 023 947, a method for structural elucidation through an optically non-transparent barrier of a biological test object is described. In the test object, an inner structure having different dielectric properties is elucidated by means of an electromagnetic spectral analysis,
wherein the test object is positioned below an array of pulse transmitters and receivers that are arranged on a plane and connected to a computer system such that data and information are transmitted,
wherein electromagnetic pulses in the spectral range of 0.01 to 1 THz are emitted onto the positioned test object by the pulse transmitters,
wherein the radiation emitted from the test object is recorded by the receivers and supplied to the computer via the data- and information-transmitting connections for an imaging process.

Since the THz radiation is very weak, long measurement times occur which are a hindrance to performing a rapid sex determination. In addition, a high absorption of accompanying water vapor in the THz range requires an extremely low and consistent humidity in the hatchery, which in turn results in considerable additional technical work.

In the document DE 20 2013 011 765 U1, a spectrophotometric analysis of the feather color of chicken embryos is described. Electromagnetic energy with a wavelength between approximately 380 nm and 740 nm is thereby used for the non-invasive sex determination of bird embryos, wherein a bird egg is exposed to the electromagnetic energy and the amount of absorption, diffusion, refraction, reflection, or any desired combination thereof of the electromagnetic energy is determined through the bird egg. By means of the presence or absence of color pigment in the interior of the bird egg, the sex of the bird embryo is at least partially determined.

The spectrophotometric analysis of the feather color of chicken eggs can only be used on brown breeds or on breeds with a color difference between female chicks and male chicks.

A summary of the disadvantages of the methods from the documents cited is provided below:
1. The sex determination at day "zero" requires access to the identified position of the germinal disc, which from previous experience entails an impairment of embryonic development and markedly decreasing hatching rates.
2. In the case of late-stage sex determination at 7 to 21 days of incubation, firstly aspects of animal welfare legislation play a role;
   wherein the bird embryo begins to experience pain starting on the seventh incubation day, and
   wherein a late-stage killing of highly developed bird embryos is carried out, since the egg contents comprise the bird embryo itself as incubation progresses;
   and secondly economic aspects play a role;
   wherein the male eggs are in the incubator longer for late-stage sex determination, which causes a substantially poorer capacity utilization of the incubators and therefore higher energy costs.
3. In the case of a sex determination using an extraction of sample material, the following problems may occur:
   the additional cleaning and disinfection required after each measurement and/or the replacement of devices or device parts (e.g. tubes) increases ongoing consumption costs considerably,
   an automation capability is more limited than for non-contact methods, and
   the risk of infection is markedly increased, as a result of which there may be a danger of reduced hatching rates.

Figure 1:
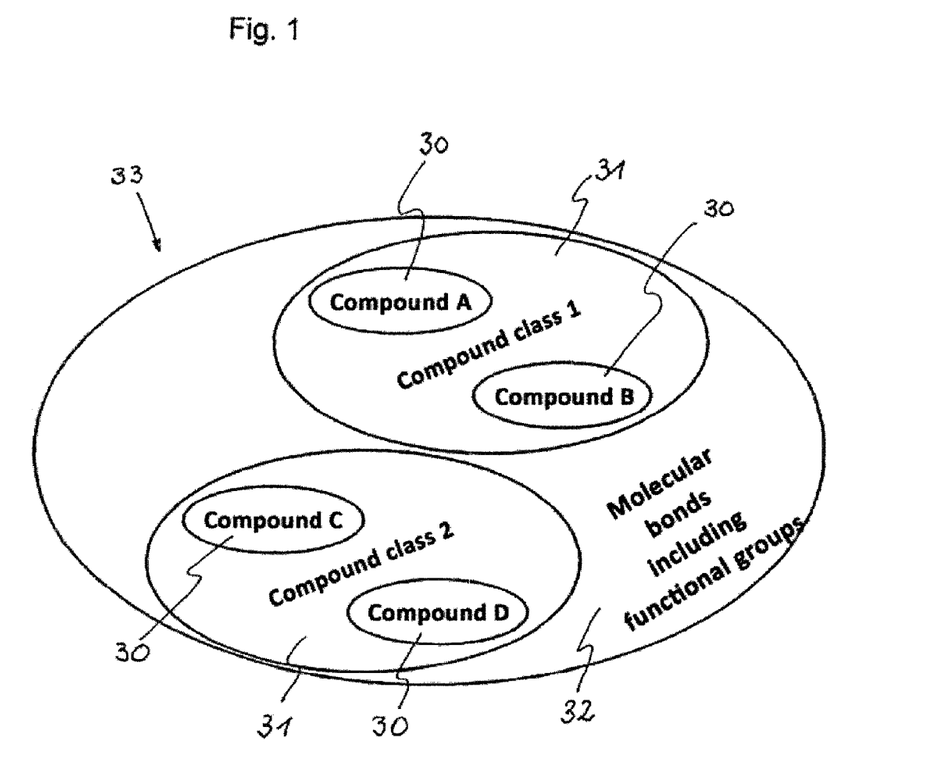
FIG. 1 An illustration of the difference between the determination levels (compound, compound classes) from the prior art and the invention level (molecular bonds including functional groups)

All of the methods and devices for sex determination described in the documents cited above can be categorized within the two inner closed fields 30, 31 of the three fields 30, 31, 32 illustrated in FIG. 1 in the evaluation-level field diagram 33 shown schematically in FIG. 1. However, in the level field diagram 33, the known methods do not include the residual field 32 in which the present method according to the invention is favored.

In the document: "Vibrational imaging and microspectroscopies based on coherent anti-Stokes Raman scattering microscopy", Andreas Volkmer, J. Phys. D: Appl. Phys. 38 (2005) R59-R81 doi:10.1088/0022-3727/38/5/R01", including the references contained therein, the coherent anti-Stokes Raman scattering spectroscopy (CARS) theory is described, which is a part of non-linear Raman spectroscopy. Using CARS spectroscopy, the same molecular vibrations are analyzed as in linear Raman spectroscopy.

However, there is an important difference between linear and non-linear Raman spectroscopy with regard to the specific manner of excitation. In CARS spectroscopy, a multi-photon process is used to excite the molecular vibrations, and a coherent signal is generated. As a result, with CARS a signal is obtained which is several orders of magnitude stronger than that of the spontaneous Raman emission in linear Raman spectroscopy (factor of $10^5$), which leads to a shorter measurement time. Furthermore, the CARS signal is blue-shifted and is therefore free of fluorescence.

The excitation occurs by means of ultrafast NIR lasers, as a result of which the penetration depth is comparable to the penetration depth in NIR Raman spectroscopy and light damage is therefore minimized.

The sensitivity is not limited by the detection of the CARS photons, but rather by the differentiation between resonant and non-resonant portions of the CARS signal. Various known methods exist for separating the resonant portion by means of special configurations for exciting/collecting the light:

polarization-sensitive detection,
time-resolved detection, and
spectral and spatial phase control.

Alternatively, the Raman spectrum can be obtained from the CARS spectrum by means of a modified Kramers-Kronig transformation or using special calculation methods, based on the assumption of maximum entropy.

Various applications of high-speed CARS spectroscopy are described in the documents:
"Differentiation of biochemical component discrimination"
A. Dogariu, Y. Huang, Y. Avitzour, R. K. Murawski, and M. O. Scully, and
"Sensitive femtosecond CARS discrimination between 2,6-Dipicolinic acid and 3,5-Dipicolinic acid," Opt. Lett., Vol. 31, No. 21, 3176 (2006);
Y. Huang, A. Soroka, K. Cohen, and A. Dogariu, and "Backscattered Coherent Anti-Stokes Raman Scattering for At Range Detection of Dipicolinic Acid and Four-Wave Mixing Multiple Scattering," J. Mod. Optics Vol. 54, No. 16, 2473 (2007); and
"Detection of bacteria" D. Pestov, X. Wang, G. O. Ariunbold, R. K. Murawski, V. A. Sautenkov, A. Dogariu, A. V. Sokolov, and M. O. Scully, and
"Single-shot Detection of Bacterial Endospores via Coherent Raman Spectroscopy," Proc. Nat. Acad. Sci. USA 105, 422 (2008); and
A. Dogariu, A. Goltsov, D. Pestov, A. V. Sokolov, and M. O. Scully, and "Real-time detection of bacterial spores using Coherent anti-Stokes Raman Spectroscopy," J. Appl. Phys. 103, 036103 (2008); and
the real-time detection of explosives in the document
Coherent Anti-Stokes Raman Spectroscopy for detecting explosives in real-time, Arthur Dogariu and Alex Pidwerbetsky, Proc. of SPIE Vol. 8358, doi: 10.1117/12.919568.

The cited Raman spectroscopic method can also be demonstrated in real-time measurements using CARS spectra of blood. The CARS vibration spectra of red blood cells can be recorded in a few picoliters and milliseconds, as is described in the following documents:
A. Dogariu, A. Goltsov, and M. O. Scully, "Real-time monitoring of blood using coherent anti-Stokes Raman spectroscopy," J. Biomed. Opt. 13, 54004 (2008) and
Rinia H A, Bonn M, Vartiainen E M, Schaffer C B, Müller M: Spectroscopic analysis of the oxygenation state of hemoglobin using coherent anti-Stokes Raman scattering. J. Biomed. Opt. 11(5):050502-050502-3.

Thus, the object of the invention is to specify a method and a device for the Raman spectroscopic in ovo sex determination of fertilized and incubated birds' eggs, which method and device are embodied such that the sex can already be determined in the eggs in a rapid and reliably unequivocal manner, wherein the female embryo continues to develop normally and the female chick can be hatched.

The object is attained by the features of patent claims 1, 5 and 30. The method is used for the Raman spectroscopic in ovo sex determination of fertilized and incubated birds' eggs, wherein the developing embryo, including the extra-embryonic structures, can move in the egg and is not yet attached to the shell,
wherein according to the characterizing part of patent claim 1
the following steps are carried out:
monitoring the chronological progression of the incubation until at least one identifiable blood vessel is developed;
creating a hole in the shell at least in the proximate region of the attached blood vessel by means of a hole-creating unit using a laser or by means of mechanical perforation;
finding the blood vessels developing in the egg using a vision system and a coaxial or lateral illumination with light in the visible wavelength range;
positioning at least one blood vessel in the laser focus of a laser source, either by moving the egg or moving an objective lens;
recording the Raman scattered radiation of the irradiated blood vessel, wherein during the measurement a movement of the blood vessel out of the focus can take place by a tracking of the vessels or an objective lens,
evaluating the Raman scattered radiation in an evaluation unit,
determining the sex and displaying the sex of the embryo in the bird egg.

The creation of a hole in the shell by means of a hole-creating unit in the form of a laser or by means of mechanical perforation can be carried out at the upwards-oriented pointed end of the egg with diameters of up to 18 mm, preferably between 8 mm and 15 mm.

The light in the visible wavelength range can be white light, but the contrast is improved if blue and/or green light from a light source is used.

During the measurement, a movement of the blood vessel out of the focus can take place by a tracking of the blood vessels or the associated objective lens, activated by the monitoring vision system.

A second method is used for the Raman spectroscopic in ovo sex determination of fertilized and incubated birds' eggs, wherein the extra-embryonic structures can no longer move freely, and instead an attachment of the chorioallantoic membrane (CAM) to the shell begins, wherein according to the characterizing part of patent claim 5 the following steps are carried out:
monitoring the chronological progression of the incubation until an attachment of the chorioallantoic membrane (CAM) to the shell begins and blood vessels are already present;
identifying the blood vessel position by means of illumination using light in the visible wavelength range;
creating a hole in the shell at least in the proximate region of the attached blood vessel by means of a hole-creating unit in the form of a laser or by means of mechanical perforation;
positioning the blood vessel in the laser focus of a laser source, either by moving the egg or moving an objective lens;
recording the Raman scattered radiation at least of one irradiated blood vessel, wherein the measurement of the blood in the capillaries or in larger vessels is performed inside or beneath the chorioallantoic membrane (CAM);
evaluating the Raman scattered radiation in an evaluation unit;
determining the sex and displaying the sex of the embryo in the bird egg.

The light in the visible wavelength range can be white or blue or green or blue and green contrast-generating light from a light source.

By creating a hole in the shell by means of a laser or by means of mechanical perforation, holes with diameters of up to 5 mm, preferably between 0.1 mm and 3 mm, can be formed.

After the respective measuring procedures and method steps, a classification takes place in the evaluation unit to detect the sex of each measured incubated bird egg before the sex is displayed.

The Raman scattered radiation from blood of extra-embryonic blood vessels and/or from blood of embryonic blood vessels can thus be used for the non-invasive, in ovo sex determination in the incubated bird egg.

The following parameters are used for the Raman spectroscopy:
- excitation wavelengths of the laser light from the laser source for the Raman spectroscopy: >600 nm, e.g. HeNe laser 633 nm, solid-state laser (Nd-based, e.g. Nd:YAG laser 1064 nm; VIS NIR diode laser, e.g. 785 nm),
- coupling of the laser excitation beam directly with mirrors and/or with optical fibers,
- Raman scattered radiation measurements are conducted with the use of optical systems embodied with a large numerical aperture NA, such as microscope objective lenses or a Raman fiber probe,
- direct decoupling of the collected Raman scattered radiation with mirrors to the spectrometer or for transport with optical fibers,
- application of dispersive Raman spectrometers and Fourier transform Raman spectrometers.

Regarding the formation of the blood vessels used and the chorioallantoic membrane (CAM) developed, it can be specified in each measuring procedure that the blood vessels develop starting from the second incubation day and the embryonic blood circulates in the bloodstream by the third incubation day. This means that an immediate sex determination is expedient at a very early stage starting from the third incubation day.

During the positioning process for the bird egg, continuously back-guided Raman spectra can be recorded and supplied to an evaluation, wherein an automatic classification of the Raman scattered radiation takes place based on the spectral fingerprint of the blood.

The egg is preferably positioned on end, and a hole can be created in the region of the upwards-oriented pointed end with a hole size of 10 mm and at three incubation days. Starting from approximately the fifth day, the chorioallantoic membrane begins to adhere to the outer membrane, and a smaller hole can be created in the shell at incubation days greater than five days, wherein the hole can also be horizontal.

The hole in the shell of the egg ensures optical access to the detected blood vessel through which blood is flowing.

The laser beam is focused onto the selected blood vessel and, if necessary, the tracking is carried out automatically using an objective lens.

The output introduced from the laser source must not result in a local or global heating of the egg above 40° Celsius.

The Raman scattered radiation can preferably be recorded by an objective lens having a large numerical aperture (NA>0.3).

The Raman scattered radiation can be detected by means of a Raman fiber probe.

The detected Raman scattered radiation can be supplied to the spectrometer via fiber lines.

To evaluate the Raman bands in the evaluation unit, the range from 500 $cm^{-1}$ to 4000 $cm^{-1}$ (Raman shift) is preferably used.

The sex-specific features are contained in the Raman bands of the nucleic acids, carbohydrates, lipids and proteins, wherein the Raman bands are supplied to a mathematical analysis.

For the mathematical analysis, methods of supervised and unsupervised classification are used, wherein the sex-specific characteristics of a table of characteristics are stored.

The detected Raman scattered radiation can be corrected such that background signals due to fluorescence or other scattering processes are eliminated and the spectra are normalized in a predetermined form.

Thus, in addition to blood, the chorioallantoic membrane (CAM) permeated with capillary vessels can also be used for the sex determination.

The sex determination can be carried out at any day between the start of incubation and the hatching, preferably in relation to the development of the blood vessels at approximately the third incubation day to the fifth incubation day.

Instead of linear Raman spectroscopy, non-linear Raman spectroscopy can be used in the form of coherent anti-Stokes Raman scattering spectroscopy (CARS), wherein the CARS spectrum from the blood of the blood vessel can be recorded using the same recording configuration as for spontaneous Raman spectroscopy, with or without fiber optics.

The CARS signal can also be generated by a wide-band femtosecond laser that serves as a pump laser and as a Stokes laser.

The CARS signal can be generated by means of two laser sources, in particular by means of a wide-band laser and a narrow-band laser for the use and evaluation of multiplex CARS spectroscopy.

The CARS spectra can be used for the classification.

The resonant portion of the CARS spectrum [$Im(Chi^{(3)})$] can be separated from the non-resonant portion [$Re(Chi^{(3)})$], and only the resonant portion only can be used for the classification.

For the CARS spectroscopy, a similar classification strategy can be carried out as for the conventional Raman spectra.

As birds' eggs, primarily chicken eggs come into consideration, the sex of which eggs is determined.

The device for determining the for the Raman spectroscopic in ovo sex determination of fertilized and incubated birds' eggs uses the aforementioned methods and comprises, according to the characterizing part of patent claim 30, at least
- one egg-mounting unit;
- one blood vessel-positioning evaluation device which is connected to the egg-mounting unit;
- one radiation device with light from the visible wavelength range of a light source for detecting at least one blood vessel inside the opened shell;
- one detector for the light for detecting blood vessels, wherein the detector is connected to the blood vessel-positioning evaluation device, wherein the radiation device and the detector form at least one vision system;
- one hole-creating unit for creating a hole in the shell at least in the proximate region of the attached blood vessel;
- one device for introducing laser light into the opened shell, wherein the device is connected to at least
  - one laser source emitting the laser light, wherein the laser light is directed in a focused manner onto at least one blood vessel, one spectrometer for recording the Raman scattered radiation from the blood of the blood vessel irradiated by the laser light via at least one line, and
one control unit for XYZ-positioning of the device onto the hole created in the egg;
one sex-determination evaluation unit which is connected to the spectrometer and the blood vessel-positioning evaluation device and indicates the sex of the incubated bird egg from the processed detected Raman scattered radiation of the spectrometer.

The device according to the invention can comprise as a vision system a device for identifying the position of blood vessels inside the egg.

The device for identifying the position of a blood vessel is connected to the control unit via at least one supply and signaling line.

The device for identifying the position of a blood vessel can be connected to a height-adjustment device and the egg-mounting unit.

The device for identifying the position of a blood vessel, the height-adjustment device and the egg-mounting unit can be connected to the blood vessel-positioning evaluation device using programming means for performing a coordination of the position of the blood vessel.

The optical device can be a flexible optical fiber.

The radiation device can preferably emit green light for detecting at least one blood vessel.

The evaluation unit can comprise programming means for the sex-determination evaluation of the detected Raman scattered radiation and the detected CARS scattered radiation.

The functional principle of the device according to the invention is explained below in greater detail:

Above a detected blood vessel, a hole is created in the shell by means of a hole-creating unit. A laser is focused onto the exposed blood vessel and, from the same location, the Raman scattered radiation is collected through the hole and fed back to a spectrometer. All of this occurs under the observation, monitoring and control of the egg illuminated using visible/green light.

With a constant illumination of the egg, a time-dependent formation of at least one blood vessel and also the subsequent formation of the chorioallantoic membrane (CAM) can be monitored, so that the start of the measuring procedure for the use of the method according to the invention can be coordinated with the chronological development of the blood vessel and subsequently also of the chorioallantoic membrane (CAM).

The detection of the blood vessels, in particular in the case of white eggs, can be carried out with the use of white or green light:

First variant: From incubation day 0 on through maximally 4.5 incubation days, the blood vessel system can still move along with the embryo. After the egg is opened, the embryo and therefore the vessels sink. After a few minutes, the position of the blood vessels is stable, whereupon a measurement takes place via a larger hole of preferably approximately 10 mm.

Second variant: From incubation day 4.5 on through incubation day 21, the chorioallantoic membrane (CAM) begins to develop and the chorioallantoic membrane begins to adhere stably to the shell. The measurement can then be conducted with a smaller hole having a diameter of 0.1 mm to 4 mm.

The Raman scattered radiation is spectrally decomposed and recorded, then processed using predetermined mathematical methods and classified according to the sex.

In summary, the invention,
a method and a device for the Raman spectroscopic in ovo sex determination of birds' eggs, in particular of chicken eggs,
comprises the following steps:

In a closed and incubated egg, the position of blood vessels is determined by means of green or white or blue light, and at a predetermined site a hole is created in the shell, in which hole the Raman scattered radiation of the blood or tissue is excited behind the shell by means of laser radiation in the red or near-infrared spectral range, and the Raman scattered radiation/Raman scattered light is recorded and supplied to a spectral and statistical evaluation, and the sex is determined based on characterizing marker bands.

For the Raman spectroscopic measurements, the following measures are taken such that
the egg preferably stands upright and the hole is created in the region of the pointed end; wherein this primarily takes place at three incubation days with a hole size of 10 mm, or is also possible in a horizontal position of the egg at more than 5 days of incubation with a smaller hole;
the hole is created in the shell using a laser or using a mechanical means;
the hole in the shell ensures optical access to a blood vessel through which blood is flowing or to the chorioallantoic membrane (CAM);
the laser beam is focused onto the blood vessel and, if necessary, automatic tracking takes place (real-time tracking);
the output introduced from the laser does not result in local or global thermal damage;
the Raman scattered light is collected by an objective lens having a large numerical aperture (typical NA is >0.3);
the Raman scattered light is recorded by a Raman fiber probe;
the recorded Raman scattered light is supplied to a spectrometer;
preferably the range from 500 to 4000 $cm^{-1}$ (Raman shift) is used for the evaluation of the Raman spectra;
the sex-specific characteristics are contained in the Raman bands of various functional groups, which are contained for example in nucleic acids, lipids, carbohydrates and proteins, which bands are supplied to a mathematical analysis;
for the mathematical analysis, methods of supervised and unsupervised classification are used, wherein the sex-specific characteristics are stored in a table of characteristics;
the form of the Raman spectra is corrected such that background signals due to fluorescence or other scattering processes are eliminated and the spectra are normalized in a suitable form;
in addition to the blood, the CAM permeated with blood capillaries can also be used for the sex determination;
the sex determination can be performed at any day between the start of incubation and the hatching.

In the method according to the invention, near-infrared light with a wavelength of 785 nm (or 1064 nm) is used for the excitation of the Raman scattering.

The advantages of the sex determination according to the invention are
no impairment of hatching and the subsequent development of the chick,
a performance of the sex determination in a highly accurate manner, wherein preferably a reliable determination of the subsequently hatched chicks, in particular at a very early point, and a non-contact determination without sampling take place than has occurred in the methods and devices of the prior art.

With the method according to the invention, no information is obtained about compounds 30 according to FIG. 1, but rather only information about molecular bonds 32, independent of the compounds in which the molecular bonds 32 occur. For example: phosphate bonds can be contained in RNA, DNA, phospholipids, etc. An analysis thus takes place at the superordinate level 32 as opposed to the prior published documents constituting the implementation levels 30. In relation to the prior art, it has been determined that there are general differences from all conventional chemical-based methods (spectroscopic and non-spectroscopic):

All methods mentioned in the documents cited in the prior art detect the presence/quantity of individual specific compounds 30 and compound classes 31 (either DNA, proteins, sugars or hormones).

In the method according to the invention and in the related device, there is no focus on either a specific compound 30, nor are absolute amounts or proportions (compound classes 31) calculated in comparison to the document WO 2014/021715 A2.

Supervised classification methods are used in order to classify the entire spectrum or one or more spectral ranges as male or female, based on a training set that can be obtained in advance from known spectra or spectral ranges.

The respective optical element for the beam guidance or for the feedback beam guidance can be a flexible optical fiber.

Developments and further embodiments of the invention are specified in the additional dependent claims.

The invention is explained in greater detail by means of an exemplary embodiment with at least one drawing.

The following show:

FIG. 3 A schematic illustration of a part of the device for introducing laser light into the hole of the shell, wherein

Figure 2:
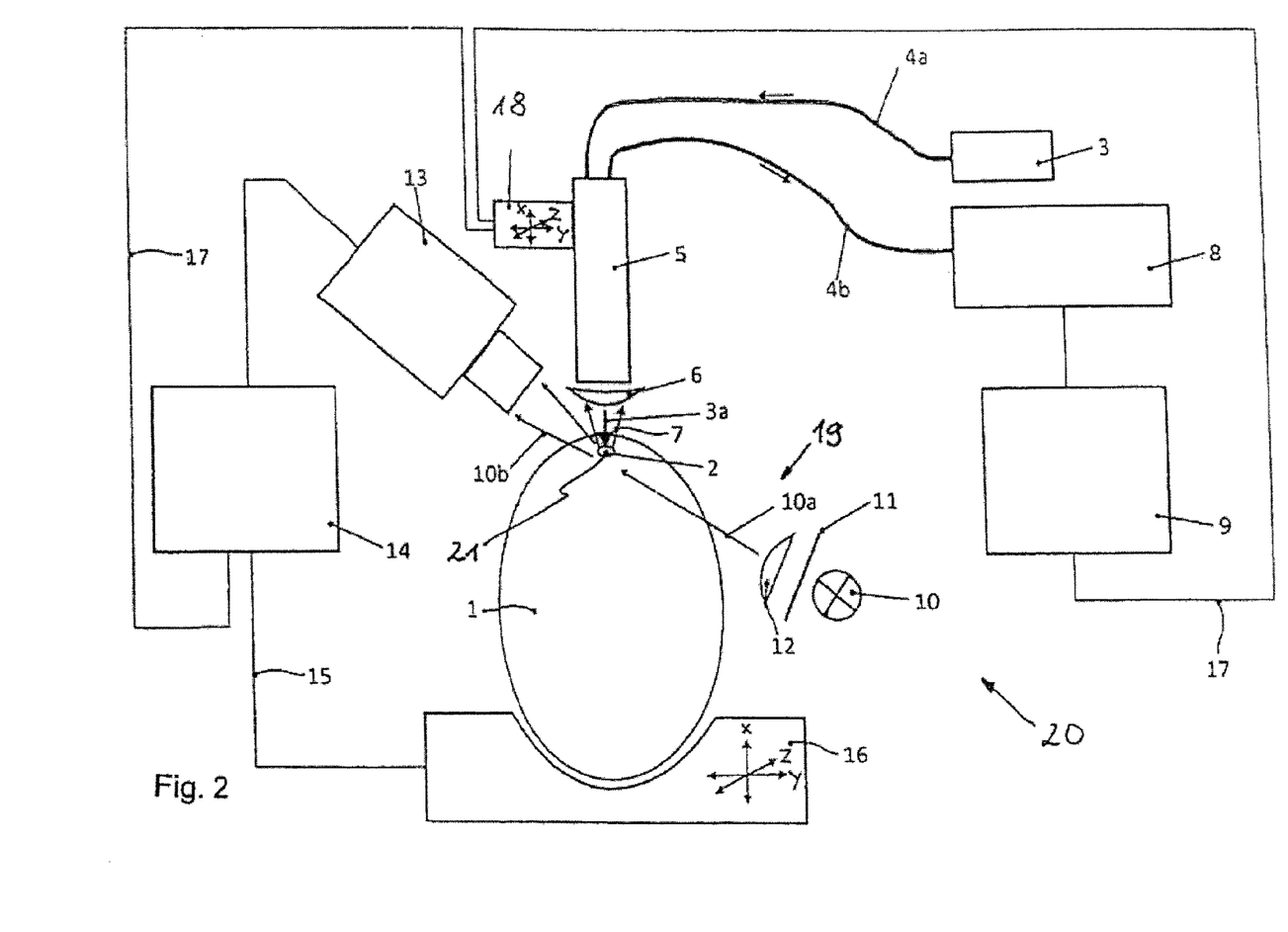
FIG. 2 A schematic illustration of the device according to the invention for determining the sex of fertilized and incubated birds' eggs.

In FIG. 2, a device 20 for the Raman spectroscopic in ovo sex determination of a fertilized and incubated bird egg 1 is shown in a schematic illustration, wherein the device 20 comprises at least
- one egg-mounting unit 16, on which the egg 1 is mounted;
- one blood vessel-positioning evaluation device 14 which is connected to the egg-mounting unit 16;
- one radiation device 19 with visible or green light 10a from a light source 10 for the detection of at least one blood vessel 21;
- one detector 13 for visible or green light 10b for the detection of blood vessels 21, wherein the detector 13 is connected to the blood vessel-positioning evaluation device 14;
- one hole-creating unit 29 for a hole 2 in the shell 28 at least in the proximate region of the attached blood vessel 21;
- one device 5 for introducing laser light 3a into the egg 1, which is connected to at least
  - one laser source 3 emitting laser light 3a and
  - one spectrometer 8 for recording the Raman scattered radiation 7 and
  - one control unit 18 for XYZ-positioning of the device 5 onto the hole 2 created in the egg 1;
- one sex-determination evaluation unit 9 which is connected to the spectrometer 8 and the blood vessel-positioning evaluation device 14 via the control unit 18.

The device 20 comprises a device 34 for identifying the position of the blood vessels 21 inside the egg 1—a vision system—in connection with the radiation device 19.

Furthermore, the device 34 includes a detector 13 in the form of a camera.

The device 34 for identifying the position of a blood vessel 21 is connected via at least one supply and signaling line 17 to the control unit 18 in the form of a coordinative positioning unit.

The device 34 for identifying the position of a blood vessel 21 is connected to a height-adjustment device (not drawn) and the egg-mounting unit 16.

The device 34 for identifying the position of the blood vessel 21, the height-adjustment device, for example inside the coordinative positioning unit 18, and the egg-mounting unit 16 can be connected in the blood vessel-positioning evaluation device 14 by programming means for a coordination and identification of the position of the blood vessel 21.

The radiation device 19 for monitoring the development of blood vessels 21, 27 can comprise the light source 10, a filter 11 and a lens 12 and can be directed at the top part of the egg 1.

The optical device 5 can be a flexible optical fiber.

Additionally, the following measures are taken such that
- the egg 1 preferably stands upright and the hole 2 is created in the region of the upwards-oriented pointed end by the hole-creating unit 29, wherein measurements are primarily possible at three incubation days with a hole size of 10 mm, and also horizontally at incubation days >5 days with a smaller hole;
- the hole 2 is created in the shell 28 using a laser 29 or using a mechanical means;
- the hole 2 in the shell 28 ensures optical access to the previously detected blood vessel 21 through which blood is flowing;
- the laser beam 3a is focused onto the blood vessel 21 inside the hole 2 and, if necessary, automatic tracking takes place;
- the output introduced from the laser source 3 does not result in local or global thermal damage to the egg 1 (temperature increase of <1° C. during measurement);
- the Raman scattered radiation 7 is recorded by an objective lens 6 having a large numerical aperture (NA>0.3);

the Raman scattered radiation 7 is recorded by a Raman fiber probe 5;

the recorded Raman scattered radiation 7 is supplied to a spectrometer 8 via a fiber line 4b;

preferably the range from 500 cm$^{-1}$ to 4000 cm$^{-1}$ (Raman shift) is used for the evaluation of the Raman bands;

the sex-specific characteristics in the Raman bands are fed to a mathematical analysis;

for the mathematical analysis, methods of supervised and unsupervised classification are used, wherein the sex-specific characteristics are stored in a table of characteristics;

the form of the Raman spectra is corrected such that background signals due to fluorescence or other scattering processes are eliminated and the spectra are normalized in a predetermined form;

membranes and fluids of the egg can also be used for enhanced sex determination;

the sex determination can be performed at any day between the start of incubation and the hatching.

Figure 3A:
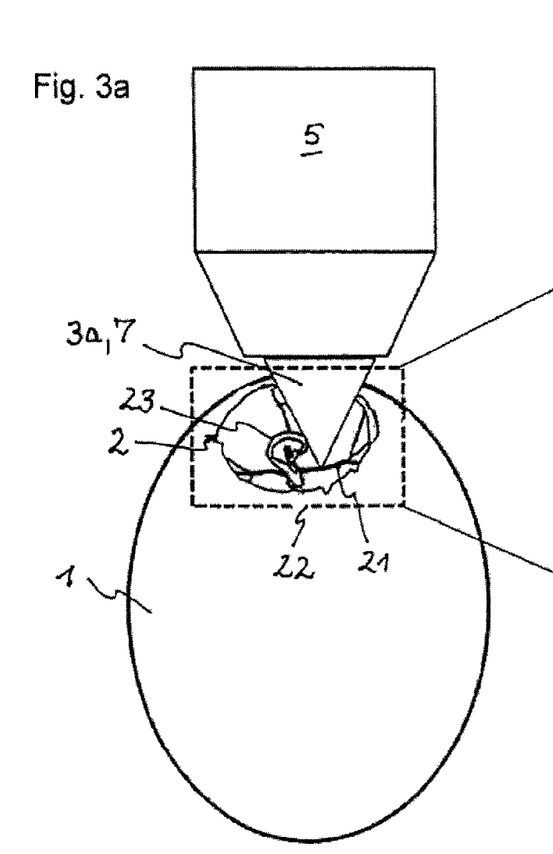
FIG. 3a shows the final part, facing the egg, for the irradiation of at least one identified blood vessel and for the detection of the Raman scattered radiation from the irradiated blood vessel.
Figure 3B:
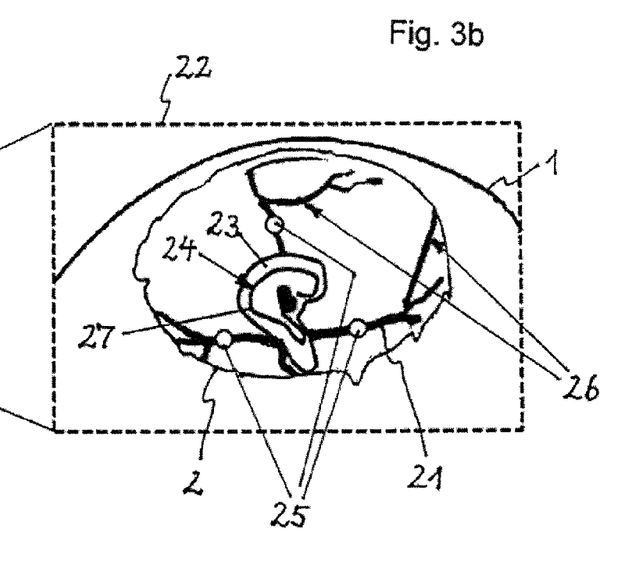
FIG. 3b shows an enlarged section with a view into the hole of the shell and with the possible measurement points on at least one blood vessel of the movable embryo.

In FIG. 3, schematic illustrations of a part of the device 5 for introducing laser light 3a into the hole 2 in the shell 28 are shown, wherein in FIG. 3a the final part, which faces the egg, for the irradiation of the at least one identified blood vessel 21 and for the detection of the Raman scattered radiation 7 originating from the irradiated blood vessel 21 is shown, and in FIG. 3b an enlarged section with a view into the hole 2 in the shell 28 and the possible measurement points on the at least one blood vessel 21 of the movable embryo 23 are shown.

In FIG. 3a, a laser light 3a focused on the blood vessel 21 is directed by the device 5. The blood vessel 21 is located outside the embryo 23. The Raman scattered radiation 7 produced is detected by the device 5 via the objective lens 6 and is transmitted. The embryo 23 also has blood vessels 27, which in FIG. 3b can likewise be the point of origin for measuring a Raman scattered radiation 7. In FIG. 3b, an enlarged section 22 of the hole 2 created in the egg 1 from FIG. 3a is shown. The embryo 23 (gray area in the hole 2), along with the embryonic blood vessels 27 thereof (shown in black), is located beneath the hole 2 in the shell 28 of the egg 1, as are multiple extra-embryonic blood vessels 21. Both blood vessels 21 and 27 can be points for the measurements and detection of the Raman scattered radiation 7, wherein the possible measurement points 24, 25, 26 can be detected depending on a chronological development of the blood vessels 21 and/or 27 and can be defined in the control and/or evaluation units 14, 9 by the programming means at least for comparison with stored Raman spectra.

Figure 4:
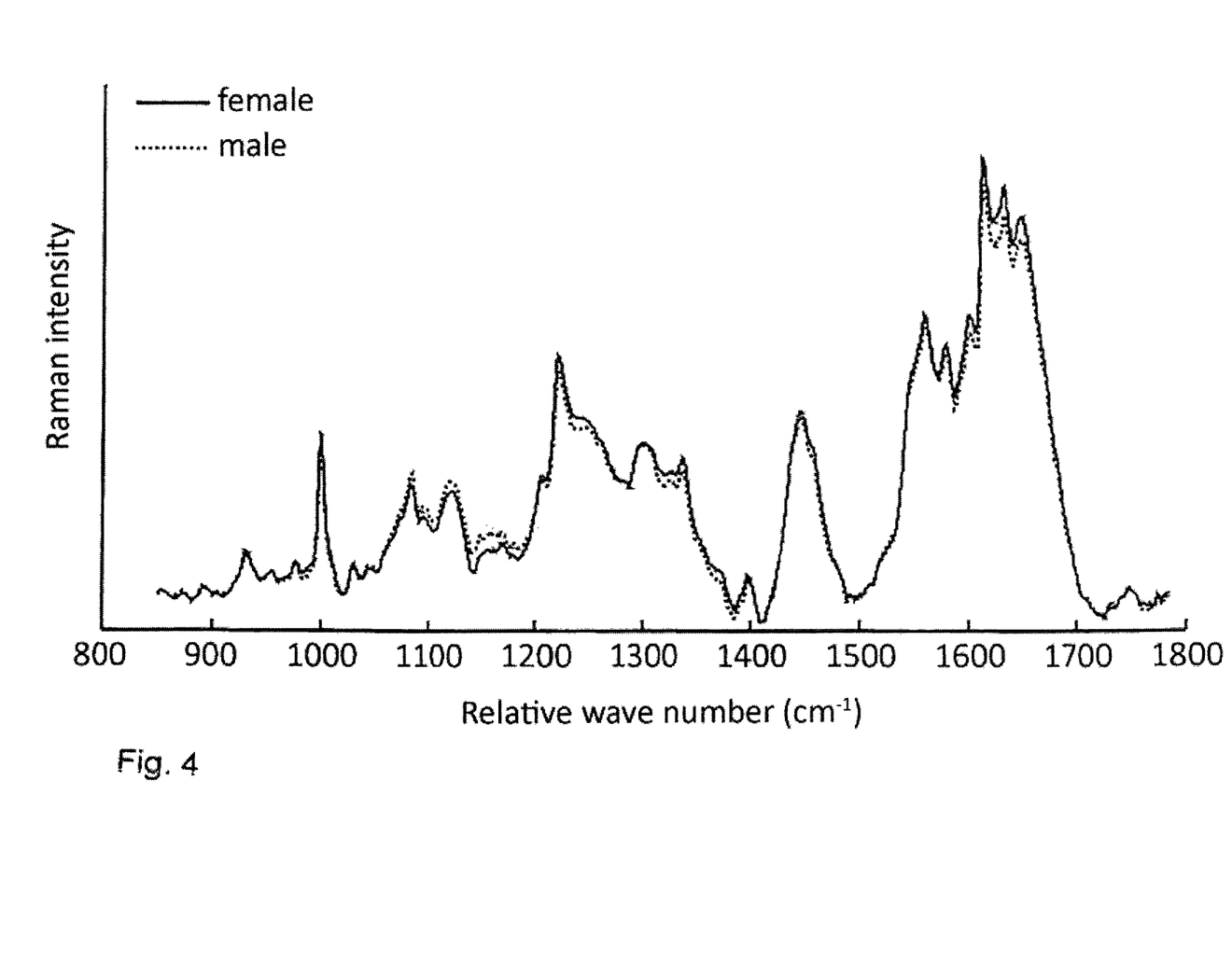
FIG. 4 A spectroscopic illustration of the evaluated Raman scattered radiation intensities in a predefined wavelength range for identifying the difference between female birds' eggs and male birds' eggs, wherein the continuous line shows the mean spectrum for the female condition and the dotted line shows the mean spectrum for the male condition.

In FIG. 4, a spectroscopic illustration of the evaluated Raman scattered radiation intensities in a predetermined wave number range of 800 cm$^{-1}$ to 1800 cm$^{-1}$ for detecting the difference between female birds' eggs and male birds' eggs is shown, wherein the continuous line shows the mean spectrum for the female condition and the dotted line shows the mean spectrum for the male condition. Between the sex curves, there are clear differences or distances in terms of the respective wave number regions between the two intensity wave number curves.

The analyses and FIG. 4 show that, for example, three to four spectral ranges may be sufficient for the sex determination, for instance, a comparison of the intensities using the absolute values can be carried out for a sex determination: for the female sex (continuous line), the intensity curve between the predetermined wave numbers is greater or less than the intensity curve for the male sex (dotted line) between the same wave numbers, as a result of which at least one intensity comparison can take place in one of the wave number ranges.

An embodiment of the light source with optical filters for the corresponding wave numbers can also be provided. In place of a costly spectrometer, at least one or more laser diode(s) or light source(s) with a wave number-related filter, in particular an interference filter related to the predefined wave numbers, can be used, wherein the wave number ν is the result of multiplying the inverse of the wavelength λ (in micrometers) by 10000.

During the sex-specific Raman scattering of the incident IR and/or NIR light, the blood from the blood vessel 21 is identified in the spectrometer 8 such that the sex of the examined bird egg 1 can be determined and displayed.

The spectroscopic evaluation takes place in the evaluation unit 9 involving mathematic classification algorithms.

Figure 5:
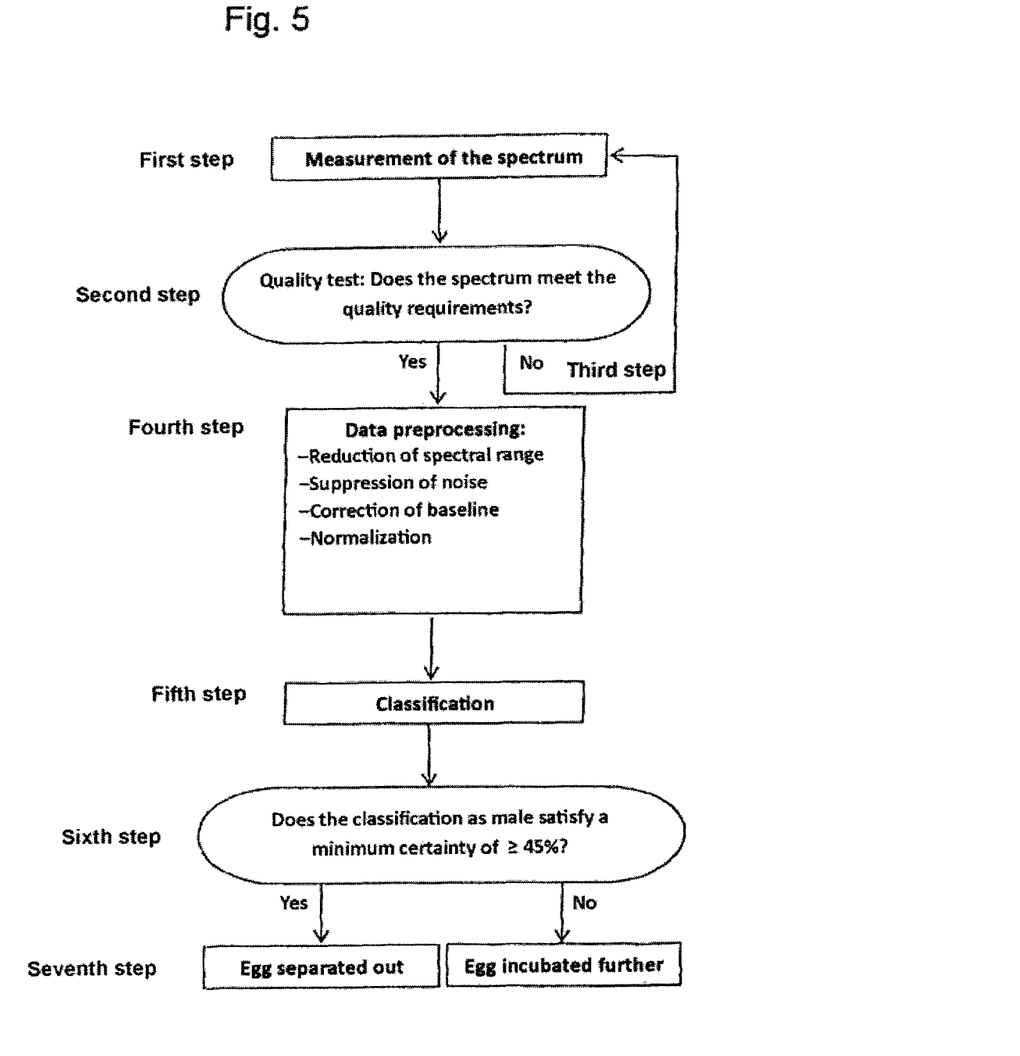
FIG. 5 A block diagram explaining the functional principle for classifying the back-guided and detected Raman spectra, and thus for the sex determination of the bird egg embryo.

In FIG. 5, the functional principle is shown including the classification of the measured Raman spectra as part of the evaluation.

For performing the spectral classification and outputting the results thereof, a multi-stage process is specified:

1. A measuring step for the Raman spectra of the egg 1 being analyzed;
2. A quality test step for the conducted measurement in order to detect the spectra and eliminate inadequately detected spectra, with which it is not possible to perform an evaluation, wherein a check whether the detected spectra satisfy the following requirements/criteria takes place:
    The ratio of the integral intensities of the $CH_2/CH_3$ stretching vibrations must match that of the blood (different from the surrounding tissue or fluids), or the ratio of the intensities of $CH_2/CH_3$ is <0.3.
    The signal-to-noise ratio (SNR) of the hemoglobin band (750 cm$^{-1}$) has at least a magnitude of 5:1.
3. A measurement repetition step, in case the two criteria of the preceding step are not met,
4. A data preprocessing step with
    a reduction of the spectral range to a wave number range between 500 cm$^{-1}$ and 4000 cm$^{-1}$,
    a suppression of the noise using a Savitzky-Golay filter,
    a correction of the baseline, for example, using a polynomial function and the correction of the offset,
    a normalizing of the spectra to an integral intensity by means of surface or vector normalization.
5. A spectral classification step with
    the application of a supervised classification. SVM—supporting vector machine, LDA—linear discriminant analysis, KNN—nearest neighbor classification or the ANN—artificial neural networks method can be used as classification methods. Other methods, such as non-linear processes/methods or supervising devices or SIMCA, can also be used. LDA classifies multiple spectral ranges, that is, the intensity values of said ranges.
6. If necessary, a verification step, wherein a reference spectra set with "male" reference spectra and "female" reference spectra having a known sexual correlation is required. The algorithm compares the spectrum with other spectra of the sex class and examines the similarity of the new spectrum with the known stored spectra.
7. A step for outputting the results of the determination of the respective sex of the birds' eggs, wherein the egg 1 is separated out if the minimum certainty for "male" of equal to or less than 45% is reached. Otherwise a female egg 1 is present which will continue to be incubated.

The method according to the invention, and the related device, use the Raman spectra preferably of blood from extra-embryonic blood vessels for the non-invasive, in ovo sex determination in the incubated bird egg 1.

The following parameters are used for the Raman spectroscopy:
- excitation wavelengths of the laser light 3a: >600 nm, e.g. HeNe laser 633 nm, solid-state laser (Nd-based, e.g. Nd:YAG laser 1064 nm; VIS NIR diode laser, e.g. 785 nm);
- coupling of the laser excitation beam 3a directly with mirrors and/or with optical fibers;
- Raman scattered radiation measurements are conducted using the optical devices 5 having a large numerical aperture, such as microscope objective lenses 6 or a Raman fiber probe 5;
- direct decoupling of the collected Raman scattered radiation 7 with mirrors to the spectrometer or for transport with optical fibers;
- application of spectrometers 8 in the form of dispersive Raman spectrometers and Fourier transform Raman spectrometers.

The following is specified for the formation of the blood vessels 21 used and the chorioallantoic membrane (CAM) developed:

The blood vessels 21 form starting at the second incubation day. At roughly the third incubation day, the embryonic blood circulates in the blood stream. Within this time span, the measurement for the sex determination is conducted.

The following two methods according to the invention are thus used:

Depending on the incubation day, two methods for measuring the Raman scattered radiation exist:
1. a section of the period of the movement of the embryo 23, and
2. a section of the period of the development of the chorioallantoic membrane (CAM) and thus the attachment of the embryo 23.

First Variant:

Until approximately the fourth incubation day, the embryo and the extra-embryonic structures can move in the egg 1, that is, they are not attached to the shell 28. The measurement procedure is carried out as follows:
- Monitoring or observing the chronological progression of the incubation until maximally the fourth incubation day;
- Creation of a hole 2 in the shell 28 by means of a laser 29 or mechanical perforation, preferably at the pointed end of the shell 28 of the egg 1 with a laser 29, having diameters of up to 18 mm, preferably between 8 mm and 15 mm;
- Finding the blood vessels 21 by means of the vision system 34, preferably using an in-line vision camera 13 and a coaxial or lateral illumination with visible light 10a from a light source 10. The visible light 10a can be white light, but the contrast is improved with blue and/or green light. The vision camera 13 records the light 10b.
- Positioning the blood vessels 21 into the laser focus of the laser source 3, either by moving the egg 1 or the objective lens 6.
- Recording the Raman scattered radiation 7, wherein during the measurement a possible movement of the blood vessel 21 out of the focus can be prevented by means of real-time tracking of the blood vessels 21 through monitoring using the vision system 34.

Preferably, a measurement occurs at the third incubation day.

Second Variant:

Starting from the fifth incubation date, the extra-embryonic structures can no longer move freely, that is, the attachment of the chorioallantoic membrane (CAM) to the shell 28 is completed. From this point of incubation on, there is a variant for the measuring procedure which is carried out as follows:
- monitoring or observing the chronological progression of the incubation from the fifth incubation day on;
- identifying the position 25, 26 of the blood vessels 21 or the position 24 of the blood vessels 27 according to FIG. 3, 3a by means of illumination with white or blue or green or blue and green light 10a;
- creating a hole 2 in the shell 28 in the region of the identified blood vessel 21, 27 by means of a laser 29 or mechanical perforation, preferably with a laser, wherein the holes 2 are formed with diameters up to 5 mm, preferably between 0.1 mm and 3 mm;
- positioning the blood vessels 21 into the laser focus, either by moving the egg 1 or moving the objective lens 6;
- recording the Raman scattered radiation 7 in the blood vessels 21, that is, a measurement of the blood in the capillaries or in larger blood vessels inside or beneath the chorioallantoic membrane (CAM) takes place.

After the respective measuring procedures, a classification takes place in the evaluation unit 9 to detect the sex of each measured incubated bird egg.

Instead of conventional linear Raman spectroscopy, non-linear CARS spectroscopy can be used for the sex determination according to the invention.

Coherent anti-Stokes Raman scattering (CARS) is part of non-linear Raman scattering. With CARS spectroscopy, the same molecular vibrations are analyzed, though the difference from (linear) Raman spectroscopy is in the specific manner of excitation. In CARS spectroscopy, a multi-photon process is used to excite the molecular vibrations, and a coherent signal is generated. As a result, with CARS a signal is obtained which is several orders of magnitude stronger than that of spontaneous Raman emission (factor of $10^5$), which leads to a shorter measurement time. Furthermore, the CARS signal is blue-shifted compared to the excitation wavelength and is therefore free of fluorescence.

The excitation occurs by means of ultrafast NIR lasers, as a result of which the penetration depth is comparable to the penetration depth in NIR Raman spectroscopy and light damage is minimized.

The sensitivity is not limited by the detection of the CARS photons, but rather by the differentiation between resonant and non-resonant portions of the CARS signal. Various methods exist for separating the resonant portion by means of special configurations for exciting/collecting the light:
- polarization-sensitive detection,
- time-resolved detection, and
- spectral phase control and spatial phase control.

Alternatively, the Raman spectrum can be obtained from the CARS spectrum by means of a modified Kramers-Kronig transformation or with special calculation methods, based on the assumption of maximum entropy.

To carry out the method according to CARS as disclosed by the invention, the following take place:
- The CARS spectrum from the blood of the blood vessel 21, 27 is detected using the same recording configuration as for spontaneous Raman spectroscopy as a function of the incubation time, with or without fiber optics;

the CARS signal can be generated by a wide-band femtosecond laser as a laser source 3, which femtosecond laser serves as a pump laser and Stokes laser;

however, the CARS signal can also be generated by two laser sources 3, a wide-band laser and a narrow-band laser (multiplex CARS);

the CARS spectra are used for the classification.

The resonant portion of the CARS spectrum [Im(Chi$^{(3)}$)] is separated from the non-resonant portion [Re(Chi$^{(3)}$)], and only the resonant portion is used for the classification.

Finally, a similar classification strategy for the CARS spectroscopy takes place as for the conventional linear Raman spectra according to the prior art.

LIST OF REFERENCE NUMERALS

1 Egg
2 Hole in the shell
3 Laser source/laser sources
3a Laser light introduced into the hole in the shell
4a Optical glass fiber conducting laser light to the egg
4b Optical glass fiber conducting Raman scattered radiation to the spectrometer/detector
5 Device for introducing the laser light into the egg/fiber probe
6 Lens for focusing the laser light and collecting the Raman scattered radiation
7 Raman scattered radiation/Raman scattered light
8 Spectrometer with detector
9 Evaluation unit
10 Light source
10a Light with which the egg is irradiated
10b Transmitted or scattered visible light
11 Green filter
12 Lens
13 Camera for the detection of light 10b
14 Blood vessel-positioning evaluation device
15 Control line
16 XYZ-positioning unit for egg position control
17 Control lines
18 Coordinative XYZ-positioning unit/control unit
19 Radiation device
20 Device according to the invention
21 Extra-embryonic blood vessel
22 Section of a shell
23 Embryo
24 Location for detecting the Raman scattered radiation of an embryonic blood vessel 27
25 Locations for detecting the Raman scattered radiation of an extra-embryonic blood vessel 21
26 Locations for detecting the Raman scattered radiation of an extra-embryonic blood vessel 21
27 Embryonic blood vessel
28 Shell
29 Hole-creating unit/laser/mechanical perforation
30 Compound field
31 Compound class field
32 Molecular bonds field
33 Detection level diagram
34 Device for identifying the position of blood vessels/vision system
35 Line

The invention claimed is:

1. A method for Raman spectroscopic in ovo sex determination of fertilized and incubated birds' eggs, wherein an embryo, including extra-embryonic structures, can move in the egg and is not yet attached to a shell at a point in time of a measurement of Raman scattered radiation, comprising:
monitoring chronological progression of incubation until at least one identifiable blood vessel develops;
creating a hole in the shell in a proximate region of an attached blood vessel by a hole-creating unit;
finding blood vessels developing in the egg using a vision system and a coaxial or lateral illumination with light in a visible wavelength range;
positioning at least one blood vessel into a laser focus of a laser source, either by moving the egg or by moving an objective lens of a device for introducing laser light and detecting the Raman scattered radiation;
recording the Raman scattered radiation of the irradiated blood vessel via the device for introducing the laser light and detecting the Raman scattered radiation, wherein during the recording, a movement of the blood vessel out of the focus can be prevented by tracking using a vision system;
evaluating the Raman scattered radiation in an evaluation unit;
determining and displaying the sex of the embryo in the bird egg.

2. The method according to claim 1,
wherein
a hole at an upwards-oriented pointed end of the egg a diameter up to 18 mm, preferably between 8 mm and 15 mm, is formed with a hole-opening device.

3. The method according to claim 1,
wherein
for the monitoring of the chronological progression of the incubation, white or blue and/or green light from a light source of a radiation device of the vision system is used as the light in the visible wavelength range.

4. The method according to claim 1,
wherein
the method for the Raman spectroscopic in ovo sex determination of fertilized and incubated birds' eggs is carried out starting from a third incubation day.

5. A method for Raman spectroscopic in ovo sex determination of fertilized and incubated birds' eggs, wherein extra-embryonic structures can no longer move freely, and wherein an attachment of a chorioallantoic membrane (CAM) to a shell begins, comprising:
monitoring a chronological progression of incubation until the attachment of the chorioallantoic membrane (CAM) to the shell begins and blood vessels are already present;
identifying a blood vessel position by illumination using light in a visible wavelength range from a light source;
creating a hole in the shell with a hole-creating unit in a form of a laser or by mechanical perforation in a proximate region of an attached blood vessel;
positioning the blood vessels into a laser focus of a laser source, either by moving the egg or an objective lens of a device for introducing laser light and detecting Raman scattered radiation;
recording the Raman scattered radiation of at least one irradiated blood vessel and measuring blood in capillaries or in larger vessels inside or beneath the chorioallantoic membrane (CAM);
evaluating the Raman scattered radiation in an evaluation unit;

determining and displaying the sex of an embryo in the bird egg.

6. The method according to claim 5, wherein
a hole with a diameter up to 5 mm, preferably between 0.1 mm and 3 mm, is formed with a hole-creating unit.

7. The method according to claim 5, wherein
for the monitoring of the chronological progression of the incubation, white or blue and/or green or blue and green light from the light source of a radiation device of a vision system is used as the light in the visible wavelength range.

8. The method according to claim 5, wherein
the method for the Raman spectroscopic in ovo sex determination of fertilized and incubated birds' eggs is carried out approximately or starting from a fifth incubation day.

9. The method according to claim 1, wherein
after the the evaluating, a classification takes place to detect the sex of each incubated bird egg before the sex is displayed.

10. The method according to claim 1, wherein
the Raman scattered radiation from blood in the blood vessels of the extra-embryonic structures and/or from blood in the blood vessels of the embryo is used for non-invasive, in ovo sex determination in the incubated bird egg.

11. The method according to claim 1, wherein
the Raman spectroscopy comprises:
excitation wavelengths of the laser light from a laser source: >600 nm (e.g., HeNe laser 633 nm, solid-state laser (Nd-based, e.g. Nd:YAG laser 1064 nm; VIS NIR diode laser, e.g. 785 nm);
coupling of the laser light directly with mirrors and/or with optical fibers (4*a*);
Raman scattered radiation measurements are conducted using optical devices having a large numerical aperture, such as microscope objective lenses or a Raman fiber probe;
direct decoupling of collected Raman scattered radiation with mirrors to a spectrometer or by transport with optical fibers;
use of a spectrometer in a form of a dispersive Raman spectrometer and Fourier transform Raman spectrometer.

12. The method according to claim 1, wherein
during the positioning, continuously back-guided Raman spectra are recorded and supplied to an evaluation, wherein an automatic classification of the Raman scattered radiation takes place based on a spectral fingerprint of the blood.

13. The method according to claim 1, wherein
the egg is positioned on end, and a hole is created in a region of a upwards-oriented pointed end of the shell with a hole size of 10 mm at three incubating days or with a smaller hole, also in a possible horizontal position, at incubation days lasting longer than five days.

14. The method according to claim 13, wherein
the hole in the shell of the egg ensures optical access to a blood vessel through which blood is flowing.

15. The method according to claim 1, wherein
the laser beam is automatically focused onto the blood vessel.

16. The method according to claim 1, wherein
an output introduced from a laser light source does not result in a local or global heating of the egg above 40° Celsius.

17. The method according to claim 1, wherein
the Raman scattered radiation is recorded by an objective lens having a large numerical aperture (NA>0.3).

18. The method according to claim 1, wherein
the Raman scattered radiation is recorded by a Raman fiber probe.

19. The method according to claim 1, wherein
the recorded Raman scattered radiation is supplied to a spectrometer via fiber lines.

20. The method according to claim 1, wherein
for evaluating Raman bands in the evaluation unit, a range from 500 cm$^{-1}$ to 4000 cm$^{-1}$ (Raman shift) is used.

21. The method according to claim 1, wherein
sex-specific features—genetic fingerprint—are contained in Raman bands of nucleic acids, carbohydrates, lipids and proteins, which bands are supplied to a mathematical analysis.

22. The method according to claim 21, wherein
for the mathematical analysis, methods of supervised and unsupervised classification are used, wherein the sex-specific characteristics are stored in a table of characteristics of the evaluation unit.

23. The method according to claim 1, wherein
a form of the Raman scattered radiation is corrected such that background signals due to fluorescence or other scattering processes are eliminated and spectra are normalized in a predetermined form.

24. The method according to claim 1, wherein
non-linear coherent anti-Stokes Raman scattering spectroscopy (CARS) is used as Raman spectroscopy, wherein CARS scattered radiation from blood of the blood vessel is recorded using a same device as for spontaneous linear Raman spectroscopy, with or without fiber optics.

25. The method according to claim 24, wherein
the CARS signal is generated by a wide-band femtosecond laser as a laser source, which femtosecond laser serves as a pump laser and as a Stokes laser.

26. The method according to claim 25, wherein
the CARS signal is generated by two lasers, by one wide-band laser and one narrow-band laser as laser sources for using and evaluating a multiplex CARS spectroscopy.

27. The method according to claim 24,
wherein
the CARS spectra are used for classification.

28. The method according to claim 24,
wherein
a resonant portion of the CARS spectrum [Im(Chi(3))] is separated from a non-resonant portion [Re(Chi(3))], and only the resonant portion is used for the classification.

29. The method according to claim 24,
wherein
for the CARS spectroscopy, a similar classification strategy is carried out as for linear Raman spectra.

30. A device for Raman spectroscopic in ovo sex determination of fertilized and incubated birds' eggs using the methods according to claim 1, comprising at least
one egg-mounting unit;
one blood vessel-positioning evaluation device which is connected to the egg-mounting unit;
one radiation device with light from a light source for detecting at least one blood vessel, wherein the radiation device irradiates at least one part of the egg;
one detector for light for detecting blood vessels, wherein the detector is connected to the blood vessel-positioning evaluation device, wherein the radiation device and the detector form at least one vision system;
one hole-creating unit for creating a hole in the shell in the proximate region of the attached blood vessel;
one device for introducing laser light into the created hole in the egg and for detecting the Raman scattered radiation, which device is connected to at least one laser source emitting the laser light, wherein the laser light is directed in a focused manner onto at least one blood vessel,
one spectrometer for recording the Raman scattered radiation from blood of the blood vessel irradiated by the laser light via at least one line, and
one control unit for XYZ-positioning of the device onto the hole created in the egg;
one sex-determination evaluation unit which is connected to the spectrometer and the blood vessel-positioning evaluation device and indicates the sex of the incubated bird egg from processed detected Raman scattered radiation of the spectrometer.

31. The device according to claim 30,
wherein
the hole-creating unit in a form of a laser or a device for mechanical perforation is connected to the blood vessel-positioning evaluation device via line.

32. The device according to claim 30,
wherein
the vision system is a device for identifying a position of the blood vessels with a detector.

33. The device according to claim 32,
wherein
the device for identifying the position of a blood vessel is connected via at least one supply and signaling line to a control unit.

34. The device according to claim 32,
wherein
the device for identifying the position of a blood vessel is connected to a height-adjustment device and the egg-mounting unit.

35. The device according to claim 32,
wherein
the device for identifying the position of the blood vessel, the height-adjustment device and the egg-mounting unit are connected in the blood vessel-positioning evaluation device, wherein a coordination of the position of the blood vessel is performed.

36. The device according to claim 30,
wherein
the optical device is a flexible optical fiber.

37. The device according to claim 30,
wherein
the radiation device emits the light in the visible wavelength range that includes at least green light for detecting at least one blood vessel.

38. The device according to claim 30,
wherein
the evaluation unit performs a sex-determination evaluation of the detected Raman scattered radiation and of detected non-linear coherent anti-Stokes Raman scattering spectroscopy (CARS) scattered radiation.

39. The device according to claim 30,
wherein
the device for introducing the laser light and detecting the Raman scattered radiation is connected to the control unit which helps the laser light to focus on the at least aone blood vessel a movable embryo.

* * * * *